United States Patent [19]

Diamond

[11] Patent Number: 4,850,864
[45] Date of Patent: Jul. 25, 1989

[54] BRACKET PLACING INSTRUMENT

[76] Inventor: Michael K. Diamond, 86 Milburn La., Roslyn, N.Y. 11577

[21] Appl. No.: 32,031

[22] Filed: Mar. 30, 1987

[51] Int. Cl.$^4$ ............................................. A61C 3/00
[52] U.S. Cl. ...................................... 433/3; 433/24; 433/72; 33/513
[58] Field of Search ............... 433/3, 72, 24, 103, 433/157, 158, 141, 9, 75; 33/513, 514

[56] References Cited

U.S. PATENT DOCUMENTS

| | | | |
|---|---|---|---|
| 1,649,664 | 11/1927 | Carter | 433/72 |
| 2,777,198 | 1/1957 | Wallace | 433/157 |
| 3,686,762 | 8/1972 | Sutter | 433/3 |
| 3,871,098 | 3/1975 | Dean | 433/3 |
| 3,906,634 | 9/1975 | Aspel | 433/72 |
| 4,035,197 | 7/1977 | Cusato | 433/3 |
| 4,063,360 | 12/1977 | Waller | 433/9 |
| 4,155,164 | 5/1979 | White | 433/3 |
| 4,250,895 | 2/1981 | Lees | 433/72 |
| 4,422,849 | 12/1983 | Diamond | 433/3 |
| 4,424,029 | 1/1984 | Maijer et al. | 433/3 |
| 4,455,138 | 6/1984 | Sheridan | 433/3 |
| 4,477,252 | 10/1984 | Lieb et al. | 433/29 |
| 4,478,576 | 10/1984 | Maijer et al. | 433/3 |
| 4,725,228 | 2/1988 | Andrews | 433/3 |

FOREIGN PATENT DOCUMENTS 2808149  5/1979  Fed. Rep. of Germany .......... 433/3
309705  9/1971  U.S.S.R. .................................. 433/72

Primary Examiner—John J. Wilson
Attorney, Agent, or Firm—Helfgott & Karas

[57] ABSTRACT

A dental apparatus for measuring the height and width of a dental surface and for placement of a bracket at an exact position with respect to the dental surface. A first pair of opposing jaws are movable for measuring the long axis of the tooth. A second pair of opposing jaws are provided for measuring the mesio-distal width of the tooth. A pair of arms are confrontingly biased and can be spread apart to grasp opposing sides of the bracket for retaining the bracket prior to placement and for subsequent release of the bracket after placement. The instrument can be included within a servo mechanism for automatic control of the placement of the bracket at a calculated position. By integrating the system with a computer, the computer can provide an image of the tooth whereby the bracket placement can be predicted on the computer and then through the servo mechanism the instrument can be instructed for proper bracket placement.

28 Claims, 9 Drawing Sheets

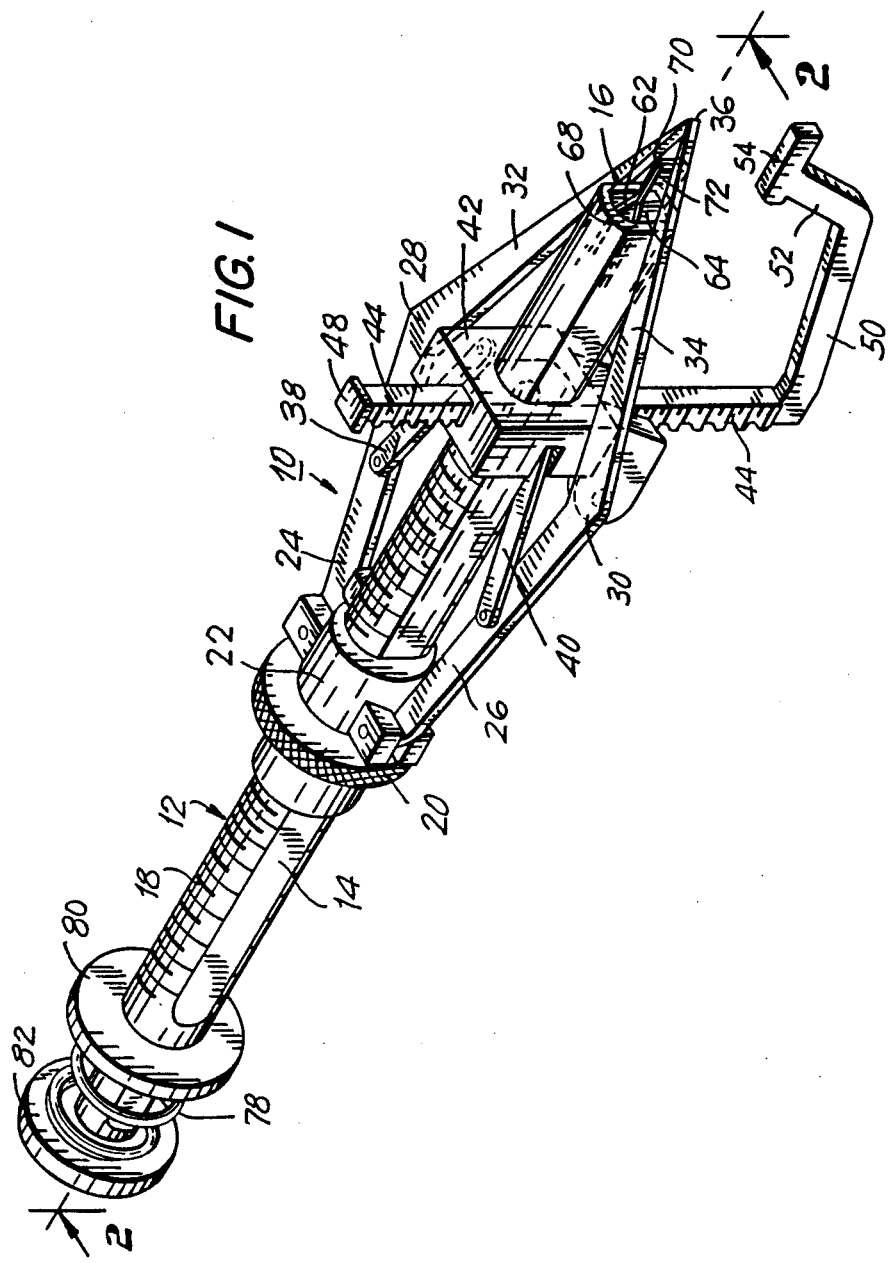

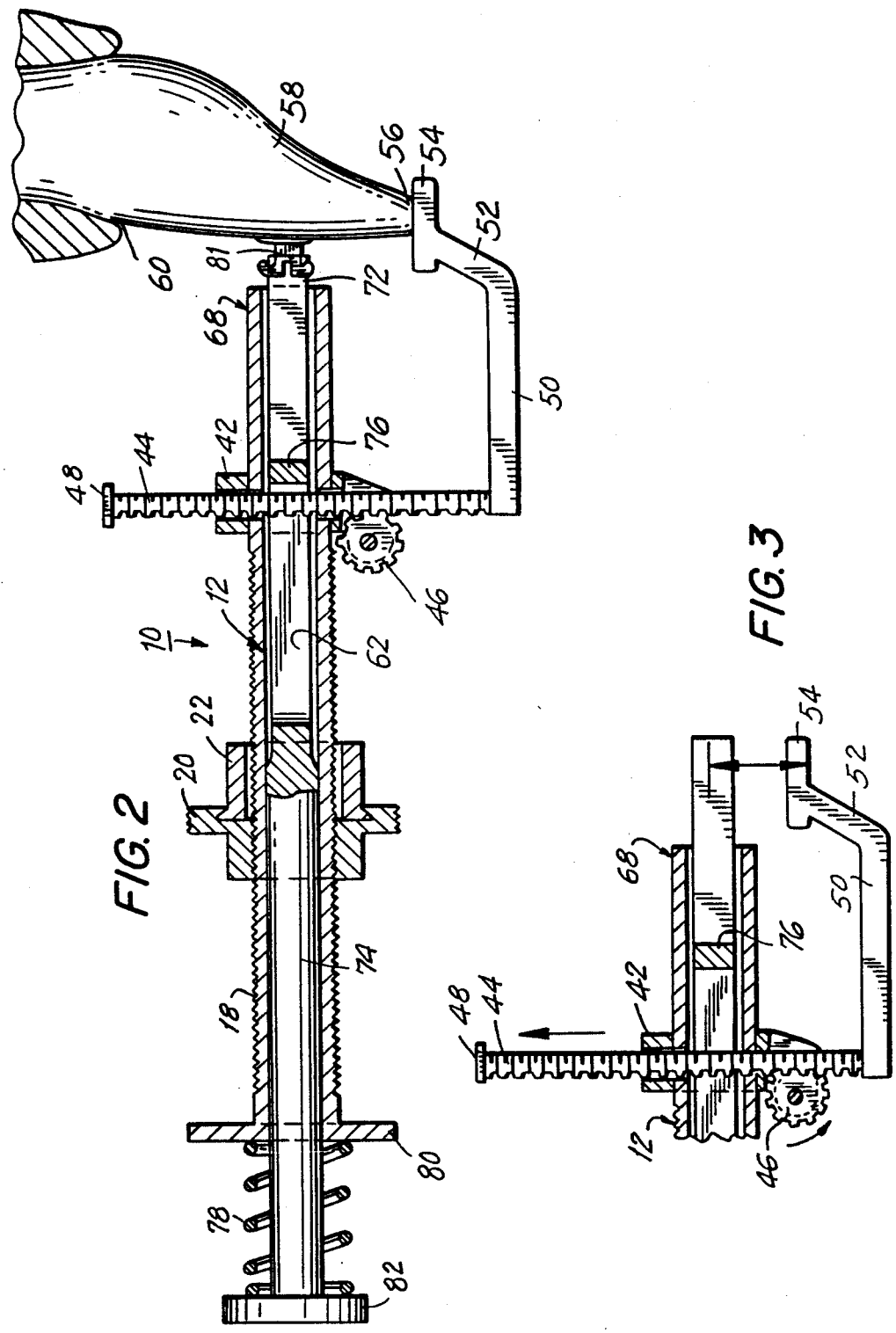

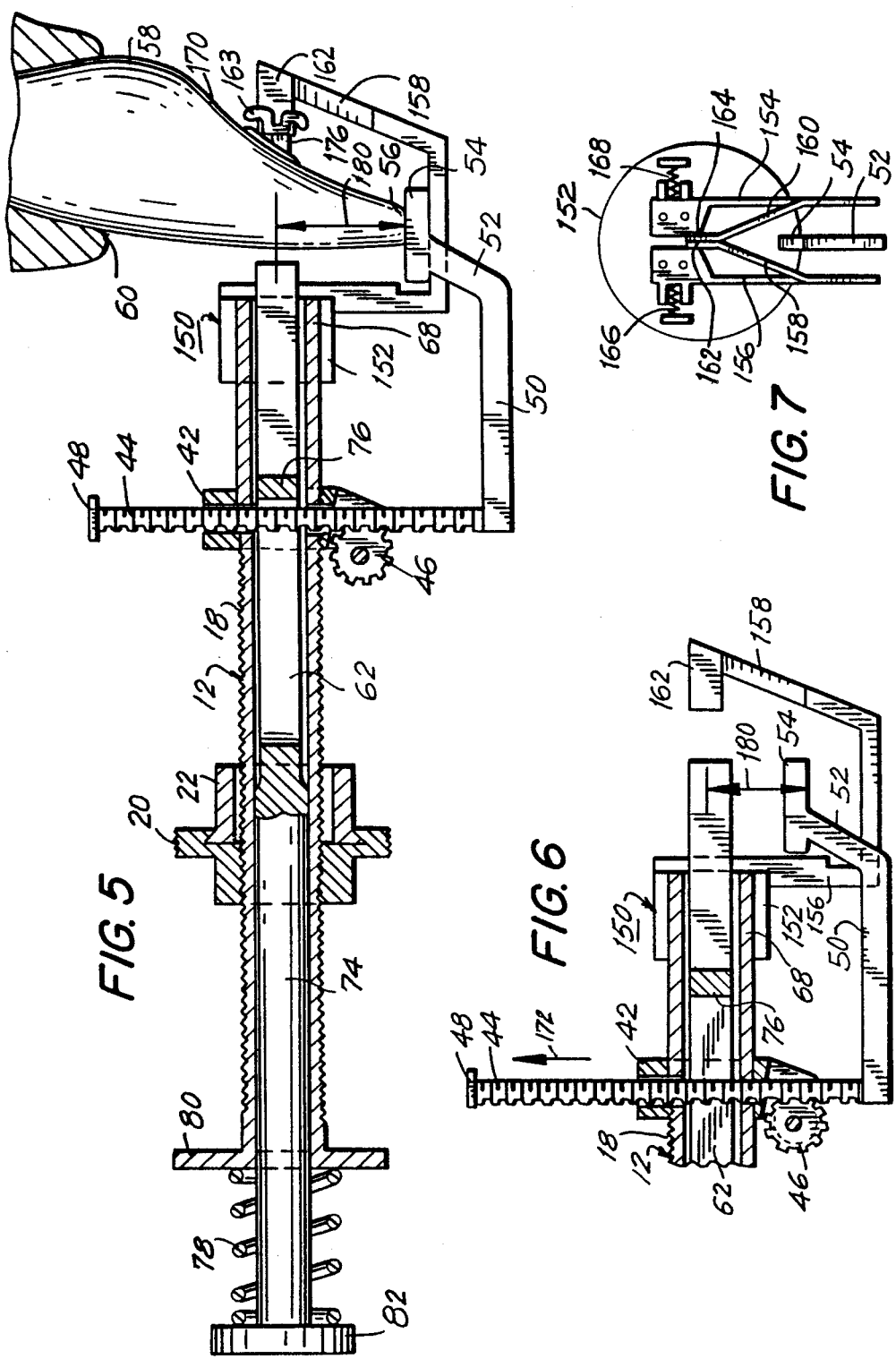

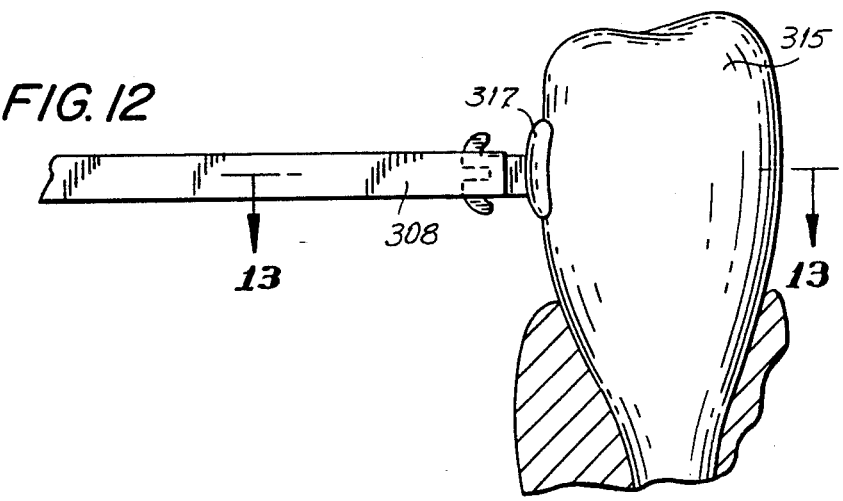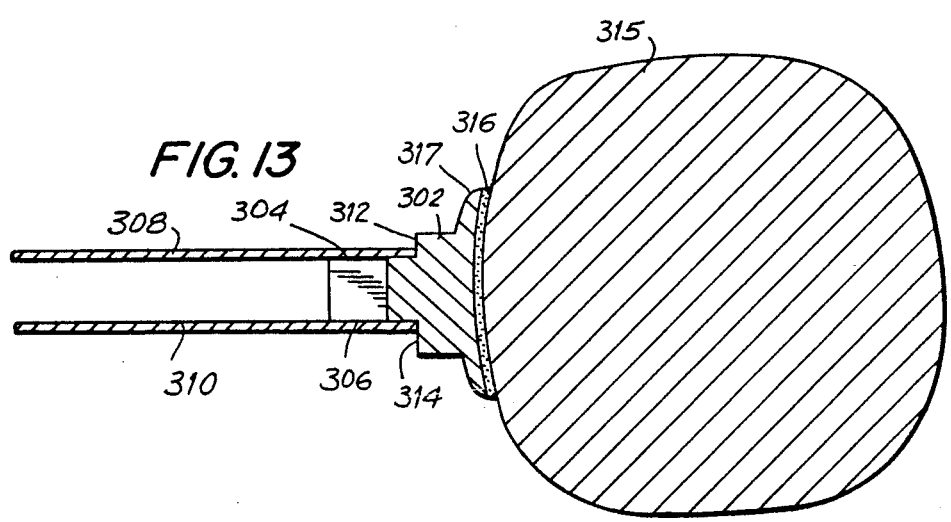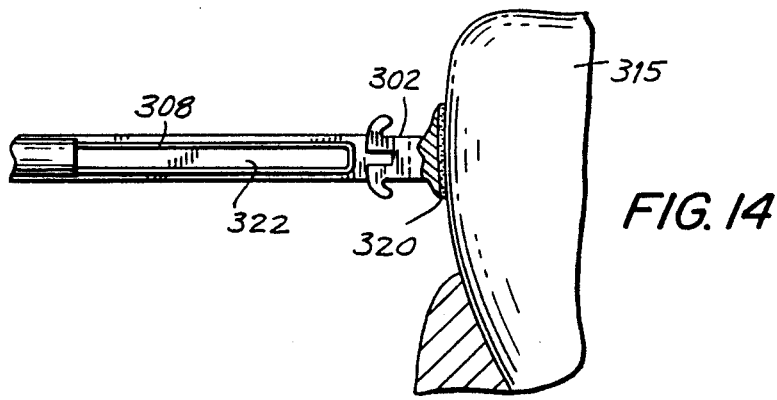

BRACKET PLACING INSTRUMENT

BACKGROUND OF THE INVENTION

This invention relates to dental apparatus, and more particularly to a dental instrument for measuring the size of a tooth and for placement of a dental bracket at an exact site location on the tooth based upon such measurement.

One of the methods of orthodontic correction is the placement of brackets on successive dental surfaces with the connection of an arch wire between the brackets. In the direct method placement, the bracket is directly secured onto a dental surface and the wires appropriately interconnected to provide the necessary torque and angulation in order to orthodontically correct the positioning of the teeth.

One of the skills of an orthodontist is to determine the appropriate position for the placement of the brackets. There are numerous recommendations as to appropriate positioning of the brackets. Some suggest that the arch wire should be constructed along the middle of the clinical crown. Others suggest placing straight guidelines parallel to the long axis of the clinical crown and then moving the bracket up and down until the middle of the slot base is at the same height as the long axis point. Some simply recommend that the bracket heights be determined according to the size and shape of the teeth without specifying an exact position. Nevertheless, at the heart of every excellent treatment result, there lies a well placed appliance.

One of the more recent recommendations is to place the bracket along the long axis of the tooth which extends from the gingival margin to the incisal edge or cusp tip. Along this axis, the suggestion is to utilize the mid point of the vertical long axis of the clinical crown.

While this, and numerous other suggestions are available, one of the key problems is to be able to provide appropriate measurements to achieve any of these particular recommended positions. At present, instruments are lacking for proper measurement of the height, width and other dimensions of the tooth in order to determine the proper midpoint for such placement. Similarly if other recommended positions are desired, they likewise require measurement of the height and width in order to determine where the desire placement position occurs. Accordingly, there is at present a need for a suitable instrument which can be utilized to make the necessary measurements of the perimetric region of the tooth surface, such as the height, width, and other such similar measurements.

While most of the bracket placement is on the facial or buccal surface, these same problems also occur with lingual orthodontic bracket placement. In fact, the problems becomes even more critical when the brackets are lingually positioned.

With regard to the actual placement of the bracket, even if a desired location were to be known, there are few instruments which have been thus far provided for bracket placement. By way of example, U.S. Pat. No. 4,422,849 issued to the inventor of the present invention describes a dental instrument for positioning a lingual orthodontic bracket. The instrument includes a housing on which is positioned an arm that includes a device for releasably holding the orthodontic bracket. A level indicator is used for displaying the extent of inclination of the arm with respect to a predetermined plane, such as the cusp tip or incisor ledge of the tooth. Based upon such desired angle of inclination, the bracket can be placed at a desired lingual position on the tooth.

This concept was extended in U.S. Pat. No. 4,455,137, issued to the inventor of the present invention, which provided the ability to indicate the relative position of the placement arm with respect to a level arm. This gave further capabilities by not just limiting the placement to an angular inclination in a first plane but gave further ability for a broader range of placement positioning capabilities.

These concepts were extended not only with respect to lingual orthodontic bracket placement but even for labial placement in U.S. Pat. No. 4,474,555 issued to the inventor of the present invention. Furthermore, the above patent also provided the concept of not necessarily placing the bracket directly on the immediate tooth surface but spacing the bracket through the use of additional adhesive material whereby the bracket can be placed in spaced relationship from the actual tooth surface in order to provide a more uniform wiring capability for the orthodontic treatment.

Another type of bracket placing device is described in U.S. Pat. No. 3,871,098. In this device, an arm projects from the barrel of a housing and includes a tongue which fits into the center groove of the bracket. A second positioning arm is balanced on top of the tooth and through the use of a plunger, the holding arm retaining the bracket projects forward of the device to press the bracket into position on the tooth surface.

While these and other instruments are available for bracket placement, these instruments only do the actual placement. The problem still exists as to selecting the appropriate position and making the bracket placement at the particular desired position on the tooth surface.

Knowing the actual position at which a bracket is located not only permits an accurate orthodontic treatment, but provides other benefits. For example, knowing the exact location of a particular placement enables the replacement of a missing or lost bracket. It also allows for the change in position of a bracket that is not having the correct effect on tooth movement due to the unique anatomy of the crown or variation of the crown root long axis. It also permits a comparison of bracket placement to tooth movement with similar teeth.

The ability to measure the entire crown surface can also permit a comparison of bracket placement on right and left quadrants of similar teeth. This enables correction to be placed in bracket location due to variations in anatomy. Numerous other benefits are also available once the measurements of the tooth surface can be achieved.

Accordingly, there is a need for a suitable dental instrument which can provide the necessary measurement of the perimetric values of teeth in order to determine the surface area of the teeth, and which can suitably position a dental bracket on either the lingual or labial surface at a desired location based upon such measurement.

SUMMARY OF THE INVENTION

It is accordingly an object of the present invention to provide a dental instrument which avoids the aforementioned problems of prior dental devices.

A further object of the present invention is to provide an instrument for measuring the height and width of a dental tooth.

Another object of the present invention is to provide a dental instrument which can be used to measure the long axis of the crown of the tooth, and the mesiodistal width of the tooth at various heights of the tooth and perpendicular to the long axis of the tooth.

Yet another object of the present invention is to provide an instrument for the placement of orthodontic brackets on dental surfaces at an accurate desired location.

A further object of the present invention is to provide an instrument for placement of orthodontic brackets based upon measurements taken of the tooth and calculations of an exact location desired for such placement.

Still a further object of the present invention is to provide an instrument for placement of orthodontic brackets which instrument includes opposing arms which grab the sides of a bracket for retention of the bracket prior to its placement and releasing of the bracket by spreading apart of the arms for positioning of the bracket at the desired location.

Yet a further object of the present invention is to provide an instrument for placement of a magnetized bracket using a selectively magnetizable arm for holding and placement of the bracket at a desired exact location on the tooth surface.

Still another object of the present invention is to provide a placement device which retains the bracket prior to placement and can aid in securing the bracket by means of light cured or heat cured adhesive with the light or heat being applied from the placement device.

Yet a further object of the present invention is to provide a bracket placement system for accurate placement of a bracket through a servo control system which positions a bracket holding device at a calculated exact location with respect to a tooth surface based upon measurement of the tooth surface.

Briefly, in accordance with the present invention, there is provided an instrument for the placement of an orthodontic bracket onto a dental surface. The instrument includes a housing with a pair of arm supported from the housing. The arms are biased into a confronting relationship to be able to grasp opposing sides of a bracket for retention of the bracket prior to placement of the bracket on the dental surface. A release mechanism on the housing spreads apart the arms in order to release the bracket after the bracket has been accurately positioned at a desired location with respect to the dental surface.

Another aspect of the present invention provides a bracket placement instrument for placement of a magnetic dental bracket including a housing with an arm projecting from the housing and including a magnetizable finger for contacting at least a portion of the bracket. The finger can be magnetized to grasp the magnet prior to placement and positioning of the bracket at a desired accurate location with respect to the tooth surface. After placement the magnetism of the finger is released permiting the bracket to remain in place.

Another aspect of the present invention provides a dental instrument for measuring of the dental tooth area, and specifically the height and width of the tooth. A first pair of jaws on the instrument housing can be adjustably separable to measure the height of the tooth along the long axis of the tooth crown. A second pair of jaws on the housing are adjustably separable in order to measure the mesio-distal width of the tooth perpendicular to the long axis at various heights on the tooth crown. The measurements can be recorded either directly on the instrument, at a separate readout, or transmitted to a computer.

By further including a servo mechanism interconnected between a computer reading the measurement and the instrument, the servo mechanism can be used to accurately position the bracket at a calculated position based upon the dimensions measured, and thereby achieves a desired bracket placement position on the tooth.

The present invention further contemplates an entire bracket placement system including suitable probe mechanisms for providing the information on the peripheral size of the tooth. A computer receives the information and provides an image of the tooth. The proper location of the bracket is then calculated. Through the use of a servo control mechanism coupled to the bracket placement instrument, and under control of the computer, the bracket placement instrument is manipulated to position the bracket at the calculated location for exact and accurate placement of the bracket on the tooth surface.

The bracket placement device can be used either for labial or lingual placement of the bracket with respect to the tooth surface.

The aforementioned objects, features and advantages of the invention, will, in part, be pointed out with particularity and will, in part, become obvious from the following more detailed description of the invention, taken in conjunction with the accompanying drawings, which form an integral part thereof. be used to accurately position the bracket at a calculated position based upon the dimensions measured, and thereby achieves a desired bracket placement position on the tooth.

The present invention further contemplates an entire bracket placement system including suitable probe mechanisms for providing the information on the peripheral size of the tooth. A computer receives the information and provides an image of the tooth. The proper location of the bracket is then calculated. Through the use of a servo control mechanism coupled to the bracket placement instrument, and under control of the computer, the bracket placement instrument is manipulated to position the bracket at the calculated location for exact and accurate placement of the bracket on the tooth surface.

The bracket placement device can be used either for labial or lingual placement of the bracket with respect to the tooth surface.

The aforementioned objects, features and advantages of the invention, will, in part, be pointed out with particularity and will, in part become obvious from the following more detailed description of the invention, taken in conjunction with the accompanying drawings, which form an integral part thereof.

BRIEF DESCRIPTION OF THE DRAWINGS

In the drawings:

FIG. 1 is a perspective view of a dental measuring and bracket placement instrument, in accordance with one embodiment of the present invention, and specifically for use in connection with the manual measurement and placement of a bracket;

FIG. 2 is a cross sectional view through the instrument showing the use of the instrument in placing a bracket on a tooth at a specific location;

FIG. 3 is a cross sectional view through a portion of the instrument shown in FIG. 1 and showing the ability to vertically adjust the instrument at a desired height along the long axis of the tooth;

FIG. 5 is a cross sectional view showing the use of the instrument of FIG. 1 in connection with the placement of a lingual bracket;

FIG. 6 is a cross sectional view of a portion of the instrument shown in FIG. 5 showing the adjustment of the positioning of the instrument;

FIG. 7 is an end view of the arms of the device shown in FIGS. 5 and 6;

FIG. 12 shows the placement of a bracket using the arms of the instrument;

FIG. 13 is a cross sectional view taken along lines 13—13 in FIG. 12;

FIG. 14 shows a modification of the instrument for use with heat cured adhesives to hold the bracket in place;

In the various figures of the drawing, like reference characters designate like parts.

DESCRIPTION OF THE PREFERRED EMBODIMENTS

Figure 4:
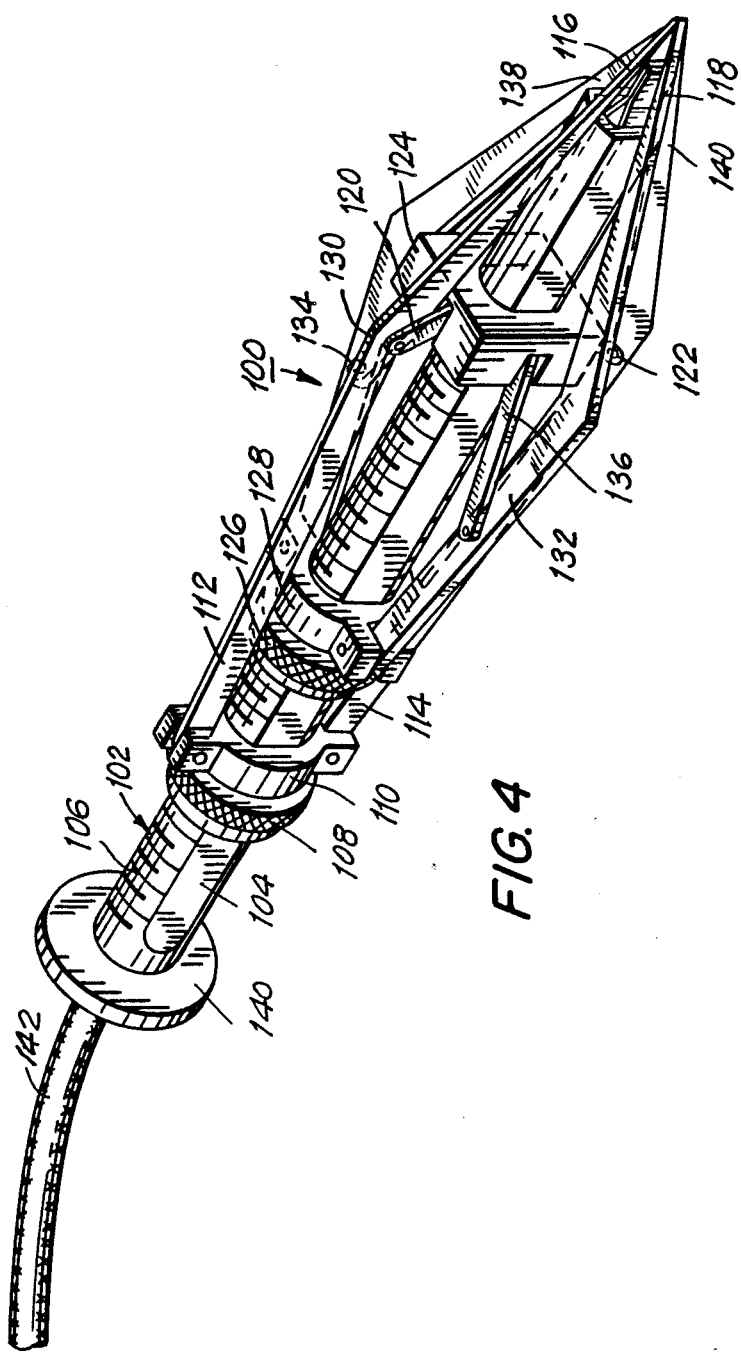
FIG. 4 is a perspective view of another embodiment of a dental measuring and bracket placement instrument, externally connected for control, readout, and manipulation of the device from a remote control unit.

The instrument of the present invention provides the ability for both measuring a tooth on which a bracket is to be placed, as well as providing an improved mechanism for the actual placement of the dental bracket on the tooth surface. Through the ability to measure the peripheral size of the tooth, it is possible to calculate the exact desired location for the placement of a bracket. By combining the capability for actual bracket placement in the same instrument that measures the tooth, it is possible to adjust the instrument to a calculated placement position and place the bracket at that position.

The tooth measurement can be achieved manually with a read out positioned directly on the instrument. The calculations of a desired position can also be done manually and then the instrument adjusted so that the instrument is positioned at the desired location and the bracket is then positioned manually.

More particularly, the instrument is capable of measuring the height of a tooth along its long axis, and specifically from the gingival margin to the incisal edge of cusp tip. The instrument can then measure the mesiodistal width of the facial or buccal surface of the crown perpendicular to the long axis of the crown at various heights, and especially at the mid point. Using the manual embodiment of the instrument, the actual values can be read out on the instrument itself. The exact mid point of the tooth can be calculated and the instrument manually adjusted so that it is positioned exactly at the midpoint. The bracket can then be loaded into the instrument and the bracket placement portion of the instrument utilized to place the bracket at this exact position.

Of course, positions can be utilized for bracket placement other than the mid point. Once the height, and width of the tooth is known, any position on the tooth can be accurately calculated and placement can be achieved at any calculated location desired.

In addition to utilizing the instrument manually, it is possible to automate the instrument and feed the measurement results into an external readout or computer. For example, rather than have the readout directly on the instrument, a readout device can be placed on a desk or technician's table. As the instrument measures the perimeter values, through a cable leading from the instrument to the readout device, the readout device can display and actually store the values in digital or analog form for the height and width measurements. The readout device can then be utilized to automatically calculate a desired placement position based upon a predetermined formula. For example, the readout device can automatically calculate the mid point based upon the height and width measurements made by the instrument.

Once the height and width have been measured and the instrument calculates the desired placement location, the instrument can then be adjusted manually. Alternatively, a servo mechanism can be connected between the instrument and the read out or control unit whereby the instrument can be automatically operated so that it positions itself at the desired location for bracket placement.

Through the use of a computer, these calculations can be easily programmed and the proper servo control can be provided. Additionally, using standard available scanning techniques, such as 3-D imaging, and using standard CAD-CAM techniques, the entire image of the tooth can be displayed on a computer readout screen. Then, using a "mouse" a desired position on the tooth surface can be selected for proper placement of a bracket. Through the use of the servo control system, the computer can then adjust the instrument so that the instrument is automatically positioned at the desired position of placement and will automatically place the bracket at this exact location.

Using a computer, the computer also can store the exact placement position with respect to the teeth and use such exact placement for further comparison or evaluation purposes. Knowing the exact placement of the bracket in each and every tooth can enable the replacement of a missing or lost bracket. It also permits storing of a profile, and a data base can be created of all such profiles for future reference. This would allow assessment and comparison bracket positioning from profile to profile.

Referring now to FIG. 1-3, there is shown one embodiment of the instrument, generally shown at 10. The instrument includes an elongated barrel shaped housing 12 having a pair of opposing flattened sides 14, 16. The barrel is externally threaded 18 to permit rotation of a circular knob 20 to achieve longitudinal movement along the length of the barrel. The knob is coupled to a yoke 22 on which are pivoted opposing arms 24, 26 of a caliper type arrangement. The arms 24, 26, are shaped with elbows 28, 30 continuing into the forward portions 32, 34 which meet at front tips 36. Through the use of the connecting linkages 38, 40, which are coupled to a block 42, the arms 32, 34 can be opened and closed through rotation of the knob 20. If desired, along the side 14 or 16 indicia can be included to provide and exact measurement of the opening size between the arms 32, 34.

Within the block 42 there is provided a rack 44 which can be moved up and down by means of a rotating pinion 46. Indicia 48 can likewise be provided along the rack so as to actually read out the height. A flat top 48 limits the downward movement.

Supported at the bottom of the rack 44 is an extending arm 50 which terminates in an upward section 52 culminating at its distal end in a lip 54. The lip 54 is designed to abut the incisal edge or cusp tip of a tooth. As shown in FIG. 3, the tip 56 of the tooth 58 abuts the lip 54 which can rest upon it.

The arms 32, 34 form a combined tip 36 which when used in combination with the lip 54 forms a first pair of measuring arms for measuring the height of the tooth. Specifically, with the lip 54 placed at the incisal edge or cusp tip, the pinion 46 is adjusted so that the rack 44 moves the combined tip 36 till it reaches the gingival margin 60, as shown in FIG. 3. This gives a measurement of the height along the long axis of the tooth. This measure of height can be measured directly on the indicia along the rack 44.

For the width measurements, the knob 20 is rotated so that the arms 32, 34 spread open until they are placed on the mesio-distal sides of the tooth to provide a reading of the width of the tooth. Such width measurements can be made at various locations. For example, it can be made at the incisal edge of the tooth, it can be made at a midpoint, or at any other position as desired along the height of the tooth.

Internally positioned within the barrel housing 12, are a pair of opposing arms 62, 64. The forward ends project from the front 68 of the housing 12 and are confrontingly positioned to defend opposing grasping fingers 70, 72. These fingers are normally biased to confront each other. The biasing can result from the shaping of the arms. In the area of the rack 44, the two arms pass on either side of the rack.

A plunger 74 with a front ram 76 axially passes through the barrel housing between the two opposing arms 62, 64. As it passes, it causes the confronting fingers 70, 72 projecting from the front end 68 of the housing to spread apart. A spring 78 is retained between an annular flange 80 at one end of the housing and a plunger knob 82 on the plunger 74. The spring 78 serves to bias the ram 74 back to its original position.

A bracket 81 can be retained between the opposing confronting fingers 70, 72 and held in position prior to placement. When the exact position of placement has been achieved, the plunger knob 82 can be depressed thereby separating the fingers 70, 72 and releasing the bracket 81 for securement onto the dental surface.

In operation, initially the height of the clinical crown of the tooth can be measured. The height can then be divided in half and the rack and pinion adjusted to the one half height position. At this point, the knob 20 is adjusted so that the mid point measurement at the half height is made. At this point, if the mid point is the desired position for bracket placement, the bracket can be loaded in place. This is achieved by pushing forward on the plunger to spread apart the fingers. The bracket is retained between the opposing fingers. The instrument is then placed adjacent the tooth. Suitable adhesive is placed on the bracket base and the plunger is again moved forward applying slight pressure on the instrument. The bracket will be accurately positioned at the exact location desired and will be secured in place. The knob is depressed again, thereby releasing the bracket which will secure in the adhesive on the tooth surface at the exact position desired.

Referring now to FIG. 4, an alternative embodiment of the instrument is shown generally at 100. The instrument includes a cylindrical barrel portion 102 having opposing flattened sides 104 and a threaded exterior 106. A first rotating knob 108 connected to a yoke 110 is provided for movement along the threaded cylindrical body in order to provide height measurements. Upper and lower scissor arms 112, 114 are pivotally connected to the yoke 110 and terminate in the opposing tips 116, 118. These are pivotally held in place by means of the linkage arms 120, 122, secured onto the block 124. Movement of the knob 108 forward and back permits opening and closing of the scissor arms 112, 114 in a vertical direction in order to measure the height along the long axis of the tooth.

A second rotating knob 126 is connected to yoke 128. A further pair of opposing scissor arms 130, 132 are held in place by means of the linkage arms 134, 136 also connected to the block 124. These scissor arms 130, 132 terminate in the pair of opposing tips 138, 140. These tips 138, 140 can be used to measure the width measurement in a manner similar to the height measurements. It should be appreciated, that in this embodiment, the height and width measurements both use the caliper or scissor type of arms. At the rear of the instrument, there is provided an enlarged flange 140. A cable 142 extends from the instrument. In this manner, the device can be automatically controlled from a servo mechanism, as will hereinafter be explained. Also, the measurements made by the instrument are transmitted through the cable 140 to a computer or other readout device separated from the instrument itself in order to provide external display and permanent recording of the measurements made.

The bracket placement portion of the instrument can be included within the device similar to that heretofore described in connection with FIGS. 1-3. For convenience, this portion is not being described in detail but it is understood it can be likewise included.

Figure 9:
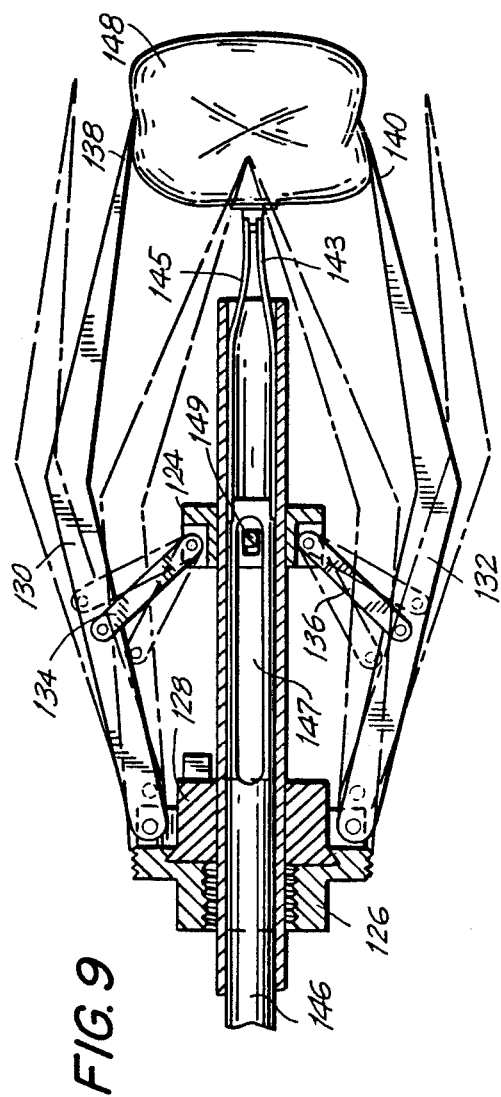
FIG. 9 is a schematic view of the operation of the device in making measurements on a tooth.

The operation of the device shown in FIG. 4 is best described as shown in FIG. 9. In order to measure a tooth 148, the rotating knobs are adjusted. Only the knob 126 is shown for convenience. This knob is used for width measurements. As the knob is moved inwardly and outwardly, the caliper or scissor arms 130, 132 are moved inwardly and outwardly, as shown in the dotted lines, to extend from the position where it forms a single tip to a position where it has outstretched arms. The portion shown in solid lines show where the tips 138, 140 are positioned along the mesio-distal sides of the tooth.

In FIG. 9, it will be noted that the plunger 146 has a slot 147 in which the center portion 149 of the block 124 can pass. This permits the plunger 146 to move even with the presence of the block 124. Movement of the plunger 146 serves to spread apart the opposing arm 145.

In the embodiment shown in FIGS. 1 and 4, with the bracket placement device extending from the front end of the instrument, the instrument is useful for placing the bracket on the labial surface of dentition. Referring to FIG. 5-7, it will be noted that with a modification, the instrument can likewise be utilized for lingual placement.

The device shown in FIGS. 5-7 is substantially identical to that shown in FIGS. 2 and 3 and is similary numbered, but includes the addition of a forward attachment shown generally at 150. The unit 150 includes a cap portion 152 which fits over the front end 68 of the barrel housing. Suitable clamping arrangements can be made to retain the cap in place. Supported from the cap 150 are a pair of opposing U-shaped arms 154, 156 which extend downdardly, then horizontally and then upwardly where the arms then approach each other at 158, 160 to terminate in the confronting tips 162, 164. The tips 162, 164 are retained in place by means of the spring tension mechanism 166, 168.

Because of the substantially U-shape of the attachment 150, it can fit underneath and around the cusp tip or incisal edge 56 of a tooth and reach onto the lingual side 170 of the tooth 58 to place a bracket 163 on the lingual surface of the dentition. Depression of the plunger knob 82 serves to spread apart the tips 162, 164 thereby permitting grasping of the bracket 163 for initial holding and also for releasing after it has been positioned in place by means of adhesive 176.

By movement of the pinion 46 on rack 44, the instrument moves upwardly along the arrow shown at 172. This adjusts the height 180 between the lower lip 54 and the bracket placement lips 162, 164 at the center of the instrument. The bracket is then grasped and positioned in place on the lingual surface.

Figure 8:
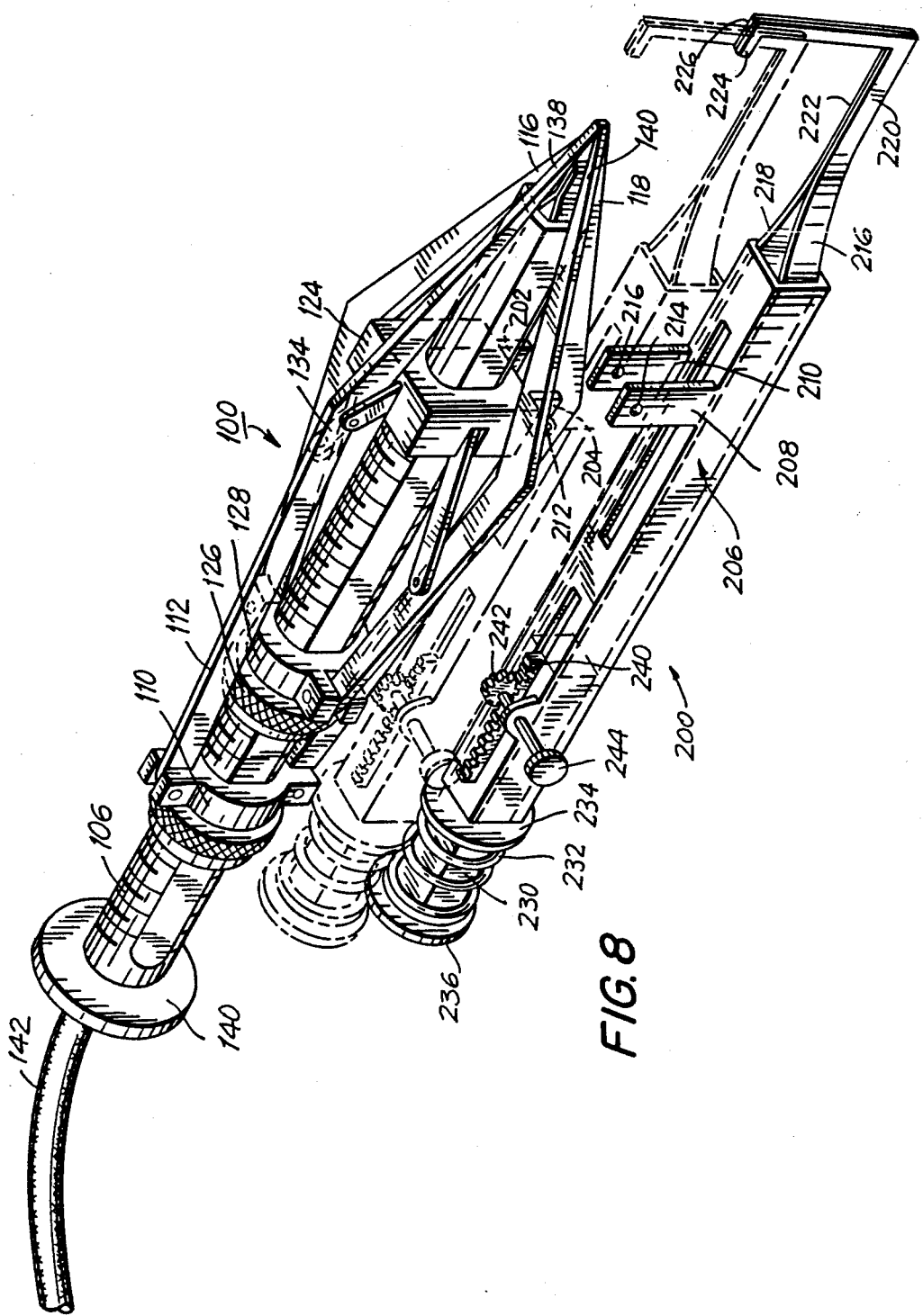
FIG. 8 is a perspective view of another embodiment of an instrument useful for lingual placement of brackets, and specifically for showing an attachment unit for use in connection with the embodiment shown in FIG. 4 to permit placement of lingual brackets.

An alternate type of lingual attachment is shown in FIG. 8. In this case, the attachment is shown as a separate unit 200 which is placed onto the unit 100 as heretofore described in connection with FIG. 4. The only modification of the unit previously shown in FIG. 4 is that a pair of grasping tabs 202, 204 project downwardly from the positioning block 124. The attachment 200 includes an elongated bar shaped housing 206 including upwardly projecting mating tabs 208, 210 for mating onto the corresponding tabs 202, 204. A plug or plunger 212 is provided to lock the tabs in place through the aligned apertures 214, 216 in the tabs 208, 210.

Internally within the bar housing 206 are a pair of opposing arms 216, 218 terminating in forward projecting portions 220, 222 which are confrontingly biased. These arm portions 220, 222 extend outwardly and upwardly terminating in the inwardly directed confronting tips 224, 226 which serve to hold the bracket.

An internal plunger 230 extends between the arms 216, 218 to spread apart the confronting tips 224, 226 holding the bracket in place on order to grasp and release the bracket. The plunger 230 is held in place by means of the biasing spring 232 held between an annular flange 234 at the end of the bar and a depressing plunger knob 236. The spring serves to return the plunger to its original position.

In order to adjust the spacing of the attachment of the thickness of the tooth, a rack 240 and pinion 242 are provided to move inwardly and outwardly housing 206. A knob 244 is provided to permit this adjustment.

In operation, the attachment portion 200, as shown in solid lines, is hooked onto the underside of the instrument 100 and connected, as shown in the dotted lines. In this position, measurements can be made on the tooth. Once an appropriate position is determined, the plunger knob 236 is depressed so as to spread apart the tips 224, 226. A bracket is placed between these tips and the knob 236 is released. The device is now positioned so that the cusp tip or incisal edge rests on the lower lip 118. The tips 224, 226 now face the lingual side and the bracket can be positioned and placed on the lingual side at the exact location desired.

Figure 11:
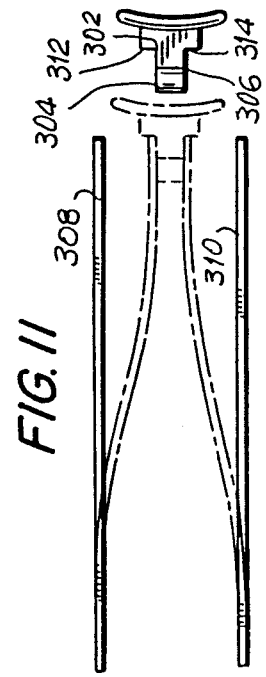
FIG. 11 is a top view of the operation shown in FIG. 10.
Figure 10:
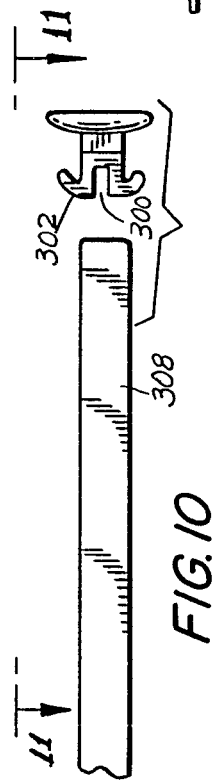
FIG. 10 is a side view showing the arms of the placement instrument ready to grasp a dental bracket.

One of the important features of the present invention is the method of grasping the bracket. This can best be seen in FIGS. 10-13. It would be noted, that normally, the method of holding a bracket is by the use of a center slot 300 provided in the bracket 302. However, in the present case, instead of using the center slot, the bracket is held by means of its opposing flat sides 304, 306. Specifically, the arms 308, 310 are initially confrontingly biased, as shown in the dotted lines in FIG. 11 and FIG. 13 so that they fit against the flat sides 304, 306 of the bracket 302 and held against the shoulders 312, 314 provided on the bracket. The arms are spread apart, as shown in their solid position in FIG. 11. The bracket is inserted between the spread apart arms. The arms are then permitted to again confront to grasp the bracket on its two sides. The bracket is then securely held in place, similar to that of the holding by a tweezer.

After the bracket has been accurately positioned with respect to the tooth 315, suitable adhesive 316 is applied and the face of the bracket 317 is moved against the adhesive on the tooth. Again the arms are spread apart to release the bracket and the bracket remains in place, secured by means of the adhesive onto the tooth 315 and bracket 317.

With the present invention, it should be appreciated that further modifications can be made. For example, the bracket can be made of magnetic material. In fact, it need not be made entirely of magnetic material but at least some portion thereof can be magnetized. Then, instead of using a pair of opposing arms, a single arm can be utilized. The arm can be made as part of an electromagnet. When the arm is energized, it will grasp the magnetic portion of the bracket and hold the bracket in place. When the arm is demagnetized, or reverse magnetized, it will release the magnetized portion of the bracket.

In this way, even using a single arm, the arm can be magnetized and used to retain the magnetized portion of the bracket. The arm is then demagnetized and the bracket is released for securement in position.

Using the pair of arms as heretofore described in connection with FIGS. 10-13, various types of adhesive material can also be utilized. For example, heat sensitive adhesive 320, can be used as shown in FIG. 14. In this case, a heat supply, such as a heated resistance wire 322 can be placed along one or both of the arms 308, 310. After the bracket is positioned in place, the resistance 312 is heated up causing the heat to be transferred to the heat sensitive adhesive 320 thereby curing the adhesive. The bracket will then be secured in place by means of the heat cured adhesive. The resistance can then be cooled and the bracket will remain in place.

Figure 15:
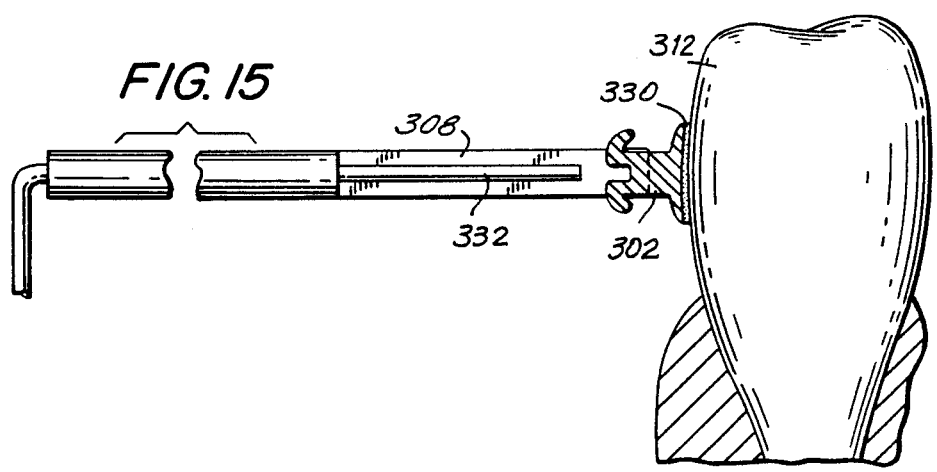
FIG. 15 is a modification for use with light cured adhesives for holding the bracket.

Likewise, instead of utilizing a heat curing adhesive, a light cured adhesive can be used, as shown in FIG. 15. In this case, the adhesive 330 retains the bracket 302 in place. A light transmitting element 332, such as a fiberoptic, can be placed along one or both the arms 308. This will transmit light towards the adhesive to cure the adhesive and thereby permit securement of the bracket in place on the tooth.

Figure 16:
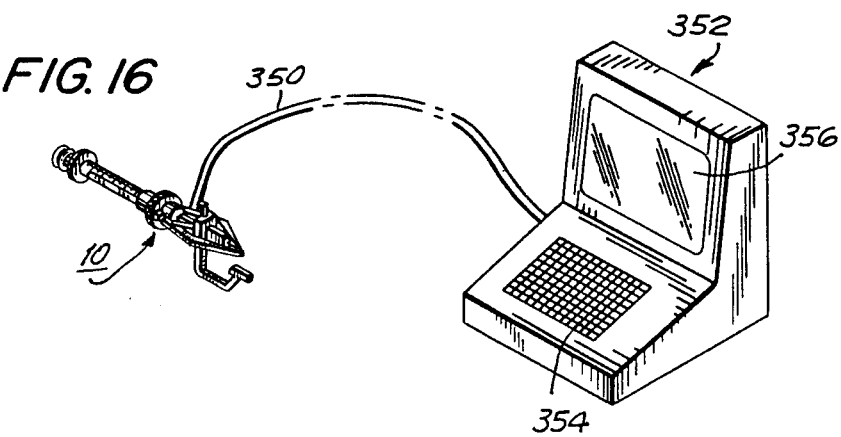
FIG. 16 is a schematic perspective view showing an external readout and control system coupled to the device shown in FIG. 1.

Referring to FIG. 16, the instrument 10 of FIG. 1, is shown connected by means of a cable 350 to a computer type control panel 352. There is provided a keyboard 354 and a screen 356. The instrument 352 can be used as a digital readout device whereby all the measurements made by the instrument 10 of the height and width can be read out, displayed, and permanently recorded. The instrument can also be utilized for calculation of the desired height and width location for the placement of the bracket.

Figure 17:
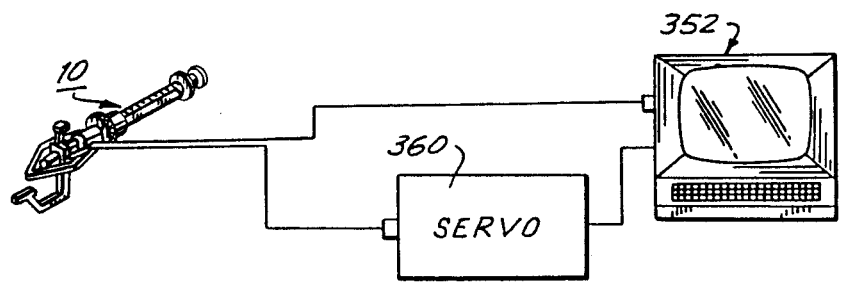
FIG. 17 is a schematic view showing a system for servo control of the measuring and bracket placement instrument using a computer system for calculation of the exact position of placement.

The instrument can be further sophisticated as shown in FIG. 17 by the use of the computer 352, with the further addition of a servo mechanism 360. In this case, not only does the information from the device 10 read to the computer 352, however, after the computer 352 has determined the appropriate position for placing the instrument, it gives control signals to the servo control mechanism 360 for automatically moving the arms on the device 10 so that it is automatically positioned at a proper placement location for the bracket.

Figure 19:
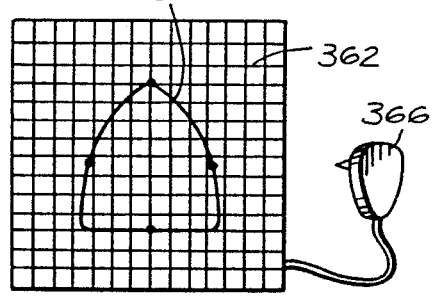
FIG. 19 is a schematic view showing the screen of a computer on which a tooth has been imaged in order to calculate the desired location for placement of the bracket.

The system of FIG. 17 can be further enhanced by the use of standard, well known CAD-CAM mechanisms. In this case, various probes, sensing devices, or 3-D imaging techniques can be utilized whereby the entire tooth can be imaged on the screen. FIG. 19 shows such a screen 362 on which a tooth 364 has been imaged or outlined by means of standard well known techniques. Through the use of a "mouse" 366, the measurement of the width, height and other parameters can be determined. Then, with the mouse 366, the appropriate position of the bracket can also be determined. Using the servo mechanism shown in FIG. 17, the instrument can be controlled for proper bracket placement in accordance with that determined on the screen of the computer.

This permits changing and alternating the position of the bracket. In fact, the image can be of a string of teeth wherein the wires can also be indicated on the teeth and thereby proper placement of the wires from bracket to bracket can be included. Bracket placement can then be modified prior to actual placement on the teeth by using the computer as the initial device for testing the forces, torque, etc., that will be achieved with the particular bracket placements.

Figure 18:
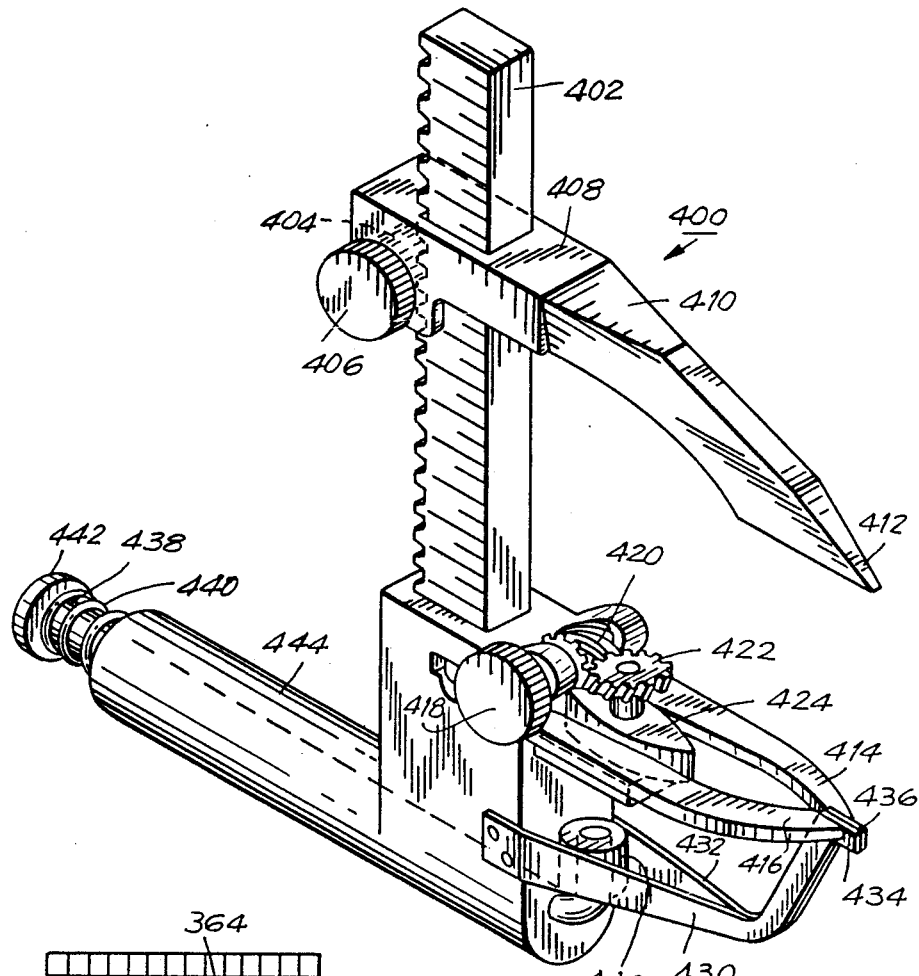
FIG. 18 is a perspective view showing another embodiment of the dental measuring and bracket placement instrument.

FIG. 18 shows yet a further modification of the device for measuring and placement of a bracket. The device is shown generally at 400 and includes a rack 402 on which is mounted a rotating pinion 404 controlled by means of knob 406. The upper housing block 408 coupled to the pinion moves up and down along the rack 402 and supports a top arm 410 with a forward distal lip 412 which would be placed at the cusp tip or the distal edge of the tooth.

The opposing arms 414, 416 which are used to measure width, can be confrontingly mated so as to form a point which would be used in opposition to the lip 412 in measuring height. These confronting arms would be placed at the gingival margin and thereby the height measured by means of adjusting the knob 406.

After the height has been measured, the arms 414, 416 can be spread apart by means of rotating the knob 418. Such rotation operates the screw 420 turning the gear 422 which in turn rotates the oval member 424 to spread apart the arms 414, 416. In this way, width measurements can be made on the tooth.

The opposing arms for grasping the bracket are shown as the confronting arms 430, 432 which terminate in the confronting tips 434, 436 which would hold opposing sides of the brackets. A plunger 438 is spring biased in its normal retracted position by means of the spring 440 held between knob 442 and housing 444, keeps the plunger in its retracted position. Upon depression of the knob 442, the plunger 438 extends through the barrel portion 444 of the housing causing its forward roller ram 446 to spread apart the arms 430, 432 thereby permitting grasping of the bracket as well as releasing of the bracket.

It will be understood, that the operation of the instrument shown FIG. 18 is substantially similar to that shown heretofore with respect to the instrument FIGS. 1 and 4. However, it shows various modifications which may be made while retaining the concept of the present invention.

It should be appreciated that the instrument is of a size that can be easily held in the hand by the technician or dentist. Measurements can be easily made in a quick and efficient manner. The measurements can either be read directly on the device, on a digital readout or fed into a computer. Once the measurements are made, the calculations can be done either manually, or as part of the instrumentation or programming which automatically provides a calculation of position as desired by the dentist. The device can then be either manually adjusted for proper bracket placement, or using the servo mechanism and computer the device can be automatically controlled to be positioned for proper placement.

In the enhanced versions, using imaging techniques, and using software programs on the computer, the measuring aspects of the present invention and the exact positioning of the bracket placement lend itself to providing programs for use with standard CAD-CAM techniques to achieve approved orthodontic placement of braces, bracket, and similar devices, both labially and lingually in order to improve the entire field of orthodontic appliance placement.

There has been described heretofore the best embodiment of the invention presently contemplated. However, it should be understood that various modifications and changes may be made without departing from the spirit of the invention.

I claim:

1. An instrument for the placement of orthodontic brackets on dental surfaces comprising:

a housing;

a pair of arms supported by the housing, means for biasing the arms into a confronting relationship to grab opposing sides of a bracket for retention of the bracket prior to its placement on a dental surface;

adjustable means on said housing for positioning the arms at any desired horizontal and vertical location with respect to the dental surface and not dependent on the dental cusp alone, for exact placement of the bracket at the desired location on the dental surface and release means on the housing for spreading both arms equidistantly apart from the desired location to release the bracket upon its being positioned at the desired location with respect to the dental surface.

2. An instrument as in claim 1, wherein said arms comprise an extension arm portion for reaching about the tooth edge for placement of a bracket onto a lingual dental surface.

3. An instrument as in claim 1, and further comprising means for measuring the height and width of the dental surface with the housing maintained in the same orientation.

4. An instrument as in cliam 3, wherein said measuring means comprise first means for measuring the long axis of the dental surface from the gingival margin to the tip of the tooth, and second means for measuring the mesio-distal width of the dental surface perpendicular to the long axis.

5. An instrument as in claim 1, wherein the bracket is retained on the dental surface through heat cured adhesive, and further comprising heating means operationally associated with said arms for directing heat to the adhesive used to secure the bracket.

6. An instrument for the placement of orthodontic brackets on dental surfaces comprising:
   a housing;
   a pair of arms supported by the housing, means for biasing the arms into a confronting relationship to grab opposing sides of a bracket for retention of the bracket prior to its placement on a dental surface;
   means on said housing for positioning the arms with respect to the dental surface for exact placement of the bracket at a desired location along a vertical line on the dental surface, and
   release means on the housing for spreading both the arms equidistantly apart from the vertical line to release the bracket upon its being positioned at a desired location with respect to the dental surface, wherein said housing comprises an elongated barrel, said arms extending longitudinally through said barrel, the distal ends of said arms projecting longitudinally therefrom, said arms being shaped to have said distal ends confrontingly biased to defing a pair of opposing clamping fingers, and a release plunger mounted in said barrel for longitudinal movement between said arms toward the dental surface to separate said clamping fingers.

7. An instrument as in claim 6, and comprising spring means for biasing said plunger to its return position.

8. An instrument for placement of orthodontic brackets on dental surfaces comprising:
   a housing;
   a pair of arms supported by the housing, means for biasing the arms into a confronting relationship to grab opposing sides of a bracket for retention of the bracket prior to its placement on a dental surface;
   means on said housing for positioning the arms with respect to the dental surface for exact placement of the brackets at a desired location on the dental surface;
   release means on the housing for spreading the arms apart to release the bracket upon its being positioned at a desired location with respect to the dental surface, and
   wherein said positioning means comprise adjustable means for movement in at least two perpendicular planes of the dental surface.

9. An instrument as in claim 8, and further comprising servo control means coupled to said housing for automatic movement of said arms.

10. An instrument as in claim 9, and further comprising computer means for calculating the desired location of bracket placement, said computer means coupled to said servo control means for operating the servo control means causing the arms to move to the calculated desired location.

11. An instrument as in claim 8, wherein said positioning means comprise means locating the vertical long axis of the dental surface, and means for adjusting the arms at a desired height along the long axis.

12. An instrument for the placement of orthodontic brackets on dental surfaces comprising:
   a housing;
   a pair of arms supported by the housing, means for biasing the arm into a confronting relationship to grab opposing sides of a bracket for retention of the bracket prior to its placement on a dental surface, and
   release means on the housing for spreading the arms apart to release the bracket upon its being positioned at a desired location with respect to the dental surface,
   wherein the bracket is retained on the dental surface through light cured adhesive, and further comprising light transmitting means operatively associated with said arms for directing light directly to the adhesive used to secure the bracket,
   and further comprising fiber optic means on said housing providing the light to said light transmitting means.

13. An instrument for the placement of orthodontic brackets on dental surfaces comprising:
   a housing;
   a pair of arms supported by the housing, means for biasing the arms into a confronting relationship to grab opposing sides of a bracket for retention of the bracket prior to its placement on a dental surface, and
   release means on the housing for spreading the arms apart to release the bracket upon its being positioned at a desired location with respect to the dental surface,
   and further comprising sensing means for obtaining an image of the dental surface, computer means for storing the image sensed and calculating the appropriate position for placement of the brackets, and servo-control means coupled to said arms and under operative control of the computer for positioning of the arms to place the bracket at the calculated position.

14. An instrument for the placement of orthodontic brackets on dental surfaces comprising:
   a housing;
   a pair of arms supported by the housing
   means for biasing the arms into a confronting relationship to grab opposing sides of a bracket for retention of the bracket prior to its placement on a dental surface;
   means on said housing fr positioning the arms with respect to the dental surface for exact placement of the bracket at a desired location along a vertical line on the dental surface, and
   release means on the housing for spreading both the arms equidistantly apart from the vertical line to release the bracket upon its being positioned at a desired location with respect to the dental surface, and further comprising electromagnetic means capable of being energized and de-energized for thereby biasing said arms into the confronting relationship, and for releasing said arms.

15. A bracket placement instrument for placement of a magnetic dental bracket on a surface, comprising:
a housing;
arm means projecting from the housing including a finger for contacting a portion of the bracket; and
means associated with the housing for magnetizing said finger for magnetic retention of the bracket prior to its placement onto a surface and for demagnetizing said finger to release the bracket upon its being positioned at a desired location with respect to the dental surface.

16. An instrument as in claim 15, wherein said means for magnetizing comprises electromagnetic means on said housing.

17. A dental instrument for measuring the height and width of a tooth comprising:
a housing;
a first pair of jaws on said housing adjustably separable to measure the height of the tooth along the long axis of the crown of the tooth with the housing in a first orientation;
a second pair of jaws on said housing adjustably separable to measure the mesio-distal width of the tooth perpendicular to the long axis at various heights of the tooth while maintaining the housing in the same orientation, and
means for recording the measurements made by said first and second pairs of jaws.

18. An instrument as in claim 17, and comprising readout means on said housing for recording of said measurements.

19. An instrument as in claim 17, comprising a desk mountable readout means for recording of said measurements, and cable means coupling said housing and said readout means.

20. An instrument as in claim 17, and comprising computer means for recording said measurements and cable means coupling said housing and said computer means.

21. An instrument as in claim 17, wherein one of the jaws of said first pair comprises an elongated finger for resting on the incisal edge or cusp tip of the tooth.

22. An instrument as in claim 17, wherein said second pair of jaws can be confrontingly positioned to define one of the jaws of said first pair of jaws.

23. An instrument as in claim 17, and further comprising bracket placement means associated with said housing for placement of a dental bracket onto the tooth.

24. An instrument as in claim 23, and further comprising computer means for recording said measurements and calculating an appropriate position for placement of a bracket on the tooth based upon the recorded measurements, and control means operated by said computer means and coupled to said bracket placement means for placement of the bracket at the calculated position.

25. A bracket placement system for placement of a dental bracket onto a tooth surface at a calculated position, comprising:
probe means for providing information of the peripheral size of the tooth;
computer means for receiving the information and providing an image of the tooth;
means for determining the desired location of a bracket based upon the image of a tooth;
bracket placement means for placement of a bracket on the tooth; and
servo control means coupled to said bracket placement means and under control of said computer means for placement of a bracket at the desired location.

26. A system as in claim 25, wherein said probe means comprises an optical scanning means.

27. A system as in claim 25, wherein said probe means comprises an instrument for determining the height and width of a tooth.

28. A system as in claim 25, wherein said bracket placement means comprises a housing, a pair of arms supported by said housing, means for biasing the arms into a confronting relationship to grasp opposing sides of a bracket for retention of the bracket prior to placement on a dental surface, and release means on the housing for spreading the arms apart to release the bracket upon its being positioned at a desired location with respect to the dental surface.

* * * * *